United States Patent
Kwon et al.

(10) Patent No.: US 12,290,345 B2
(45) Date of Patent: May 6, 2025

(54) APPARATUS AND METHOD FOR ESTIMATING BLOOD PRESSURE

(71) Applicant: SAMSUNG ELECTRONICS CO., LTD., Suwon-si (KR)

(72) Inventors: Ui Kun Kwon, Hwaseong-si (KR); Chang Soon Park, Chungju-si (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 18/328,257

(22) Filed: Jun. 2, 2023

(65) Prior Publication Data
US 2023/0301526 A1    Sep. 28, 2023

Related U.S. Application Data

(63) Continuation of application No. 16/359,519, filed on Mar. 20, 2019, now Pat. No. 11,701,010.

(30) Foreign Application Priority Data

Aug. 20, 2018  (KR) .................. 10-2018-0096673

(51) Int. Cl.
*A61B 5/021*      (2006.01)
*A61B 5/00*       (2006.01)
(52) U.S. Cl.
CPC .......... *A61B 5/02116* (2013.01); *A61B 5/021* (2013.01); *A61B 5/02125* (2013.01);
(Continued)
(58) Field of Classification Search
CPC . A61B 5/02116; A61B 5/021; A61B 5/02125; A61B 5/681; A61B 5/7275; A61B 5/746; A61B 2560/0228
(Continued)

(56) References Cited

U.S. PATENT DOCUMENTS

| 5,931,790 A | 8/1999 | Peel, III |
| 8,282,564 B2 | 10/2012 | Parlikar et al. |

(Continued)

FOREIGN PATENT DOCUMENTS

| CN | 101327121 A | 12/2008 |
| KR | 1020160094218 A | 8/2016 |

(Continued)

OTHER PUBLICATIONS

Communication dated Jan. 8, 2020, issued by the European Patent Office in counterpart European Application No. 19192475.2.
(Continued)

*Primary Examiner* — Christine H Matthews
*Assistant Examiner* — Chanel J Jhin
(74) *Attorney, Agent, or Firm* — Sughrue Mion, PLLC

(57) ABSTRACT

An apparatus for non-invasively estimating blood pressure is provided. The apparatus for estimating blood pressure may include a bio-signal measurer configured to measure a bio-signal from a user and a processor configured to estimate blood pressure using the measured bio-signal. The processor may extract a first feature and a second feature from the bio-signal at an extraction time, estimate changes in the first feature and the second feature which have occurred during a time period from a calibration time at which the first feature and the second feature are calibrated to the extraction time at which the first feature and the second feature are extracted, and estimate a blood pressure based on the changes in the first feature and the second feature.

9 Claims, 8 Drawing Sheets

(52) U.S. Cl.
CPC ............ *A61B 5/681* (2013.01); *A61B 5/7275* (2013.01); *A61B 5/746* (2013.01); *A61B 2560/0228* (2013.01)

(58) Field of Classification Search
USPC .......................................................... 600/485
See application file for complete search history.

(56) References Cited

U.S. PATENT DOCUMENTS

| | | | |
|---|---|---|---|
| 9,375,160 | B2 | 6/2016 | Parlikar et al. |
| 10,342,496 | B2 | 7/2019 | Kang et al. |
| 10,820,864 | B2 | 11/2020 | Peterson |
| 11,344,209 | B2 * | 5/2022 | Park ................... A61B 5/02108 |
| 11,701,010 | B2 * | 7/2023 | Kwon ................. A61B 5/02116 600/485 |
| 2007/0106164 | A1 * | 5/2007 | Yang ...................... A61B 5/022 600/490 |
| 2008/0287812 | A1 | 11/2008 | Parlikar et al. |
| 2012/0136261 | A1 * | 5/2012 | Sethi .................. A61B 5/02125 600/485 |
| 2013/0006127 | A1 | 1/2013 | Parlikar et al. |
| 2014/0358015 | A1 | 12/2014 | Cohen et al. |
| 2016/0081563 | A1 | 3/2016 | Wiard et al. |
| 2016/0143546 | A1 | 5/2016 | McCombie et al. |
| 2016/0256115 | A1 | 9/2016 | Peterson |
| 2017/0112395 | A1 | 4/2017 | Kim et al. |
| 2017/0172431 | A1 | 6/2017 | Kim et al. |
| 2017/0360314 | A1 | 12/2017 | Proenca et al. |
| 2018/0177465 | A1 | 6/2018 | Kwon et al. |

FOREIGN PATENT DOCUMENTS

| | | |
|---|---|---|
| KR | 10-2017-0048970 A | 5/2017 |
| KR | 10-2017-0049870 A | 5/2017 |
| KR | 10-2017-0073051 A | 6/2017 |
| KR | 10-1746492 B1 | 6/2017 |
| KR | 10-2017-0133132 A | 12/2017 |
| KR | 10-2018-0076806 A | 7/2018 |
| KR | 10-2018-0077019 A | 7/2018 |
| WO | 9855021 A1 | 12/1998 |
| WO | 2008/144404 A1 | 11/2008 |

OTHER PUBLICATIONS

Communication dated Nov. 14, 2022 issued by the Korean Intellectual Property Office in Korean Application No. 10-2018-0096673.
Parlikar et al., "Model-Based Estimation of Cardiac Output and Total Peripheral Resistance", Computers in Cardiology, 2007, pp. 379-382, 4 total pages.
Office Action issued on Jan. 30, 2024 by the Chinese Patent Office in corresponding CN Patent Application No. 201910375976.X.

* cited by examiner

APPARATUS AND METHOD FOR ESTIMATING BLOOD PRESSURE

CROSS-REFERENCE TO RELATED APPLICATION(S)

This application is a continuation application of U.S. Ser. No. 16/359,519, filed Mar. 20, 2019, which claims priority from Korean Patent Application No. 10-2018-0096673, filed on Aug. 20, 2018 in the Korean Intellectual Property Office, the disclosures of which are incorporated herein by reference in their entireties.

BACKGROUND

1. Field

Apparatuses and methods consistent with example embodiments relate to estimating blood pressure, and more particularly to estimating blood pressure based on relative changes in cardiovascular features with respect to the time of calibration.

2. Description of Related Art

Recently, active research has been conducted on Internet technology (IT)-medical convergence technology, which is a combination of IT technology and medical technology, due to the aging population structure, rapidly growing medical expenses, and the shortage of professional medical service personnel. In particular, health monitoring systems have extended care from hospitals to patients' home and office so that the patients can monitor their health state in daily life. Archetypal examples of bio-signals indicating the individual's health status may include an electrocardiography (ECG) signal, a photoplethysmogram (PPG) signal, an electromyography (EMG) signal, and the like. Various bio-signal sensors are being developed to measure such signals in daily life. In particular, in the case of a PPG sensor, it is possible to estimate blood pressure of a human body by analyzing pulse waveforms in which a cardiovascular status is reflected.

SUMMARY

According to an aspect of an example embodiment, there is provided an apparatus for estimating blood pressure including a bio-signal measurer configured to measure a bio-signal from a user, and a processor configured to extract a first feature and a second feature from the bio-signal at an extraction time, estimate changes in the first feature and the second feature which have occurred during a time period from a calibration time at which the first feature and the second feature are calibrated to the extraction time and estimate a blood pressure based on the changes in the first feature and the second feature.

The first feature may be a cardiac output and the second feature may be a total peripheral resistance.

The processor may acquire, from the bio-signal, at least one of heartbeat information, information on a shape of a waveform of the bio-signal, area information of the waveform, time and amplitude information at a maximum point of the bio-signal, time and amplitude information at a minimum point of the bio-signal, and amplitude and time information of a constituent pulse waveform of the bio-signal, and may extract the first feature and the second feature based on the at least one information.

The processor may estimate mean arterial pressure (MAP), diastolic blood pressure (DBP), and systolic blood pressure (SBP) based on the first feature and the second feature.

The processor may calculate a first difference between an initial value of the first feature at the calibration time and a changed value of the first feature at the extraction time, calculate a second difference between an initial value of the second feature at the calibration time and a changed value of the second feature at the extraction time, calculate a product of the first difference and the second difference, and estimate the blood pressure based on the first difference, the second difference, and the product of the first difference and the second difference.

The processor may normalize each of the first difference, the second difference, and the product of the first difference and the second difference, based on at least one of the initial value of the first feature and the initial value of the second feature at the calibration time, to obtain normalization results, and estimate the blood pressure based on each of the normalization results.

The processor may apply a weight to each of the normalized results to obtain weighted results, combine the weighted results to obtain a combination result, and estimate the blood pressure by applying a scaling factor to the combination result.

The processor may determine the scaling factor based on at least one of a reference MAP, a reference SBP, and a reference DBP of the user, which are measured at the calibration time, and a result of combining the reference SBP and the reference DBP.

The processor may independently estimate MAP, SBP, and DBP by adjusting at least one of the weight and the scaling factor.

The processor may estimate MAP and estimate DBP and SBP based on the estimated MAP and a pulse pressure.

The processor may estimate MAP of the user by adjusting at least one of the weight and the scaling factor, and estimate DBP and SBP of the user based on the MAP, a pulse pressure measured from the bio-signal, and the adjusted at least one of the weight and the scaling factor.

The processor may calculate a first value and a second value based on the pulse pressure, estimate the DBP based on the MAP and the first value, and estimate the SBP based on the estimated DBP and the second value.

The apparatus may further include a communication interface configured to, when the user measures reference blood pressure for calibration through an external blood pressure measurement device at the calibration time, receive the reference blood pressure from the external blood pressure measurement device.

The bio-signal measurer may measure a bio-signal for extracting the changed value of the first feature and the changed value of the second feature from the user during measurement of the reference blood pressure.

The processor may determine whether to perform calibration according to preset criteria, and guide the user to perform calibration when it is determined that calibration is needed.

The bio-signal may include one or more of a photoplethysmogram (PPG) signal, an electrocardiography (ECG) signal, an electromyography (EMG) signal, and a ballistocardiogram (BCG) signal.

The bio-signal measurer may include a sensor configured to measure at least one of the PPG signal, the ECG signal, the EMG signal, and the BCG signal.

The apparatus may further include an output interface configured to output a result of estimating the blood pressure.

According to an aspect of another example embodiment, there is provided a method of estimating blood pressure including acquiring a bio-signal of an object at an extraction time; estimating changes in the first feature and second feature which have occurred during a time period between the extraction time and a calibration time at which the first feature and the second feature are calibrated; and estimating blood pressure based on the changes in the first feature and the second feature.

The first feature may be a cardiac output and the second feature may be a total peripheral resistance.

The extracting of the first feature and the second feature may include acquiring, from the bio-signal, at least one information of heartbeat information, information on a shape of a waveform of the bio-signal, area information of the waveform, time and amplitude information at a maximum point of the bio-signal, time and amplitude information at a minimum point of the bio-signal, and amplitude and time information of a constituent pulse waveform of the bio-signal, and extracting the first feature and the second feature based on the at least one information.

The estimating the blood pressure comprises estimating mean arterial pressure (MAP), diastolic blood pressure (DBP), and systolic blood pressure (SBP) based on the changes in the first feature and the second feature.

The estimating the changes may include calculating a first difference between an initial value of the first feature at the calibration time and a changed value of the first feature at the extraction time, calculating a second difference between an initial value of the second feature at the calibration time and a changed value of the second feature at the extraction time, and calculating a product of the first difference and the second difference.

The estimating the changes may include normalizing each of the first difference, the second difference, and the product of the first difference and the second difference based on at least one of the initial value of the first feature and the initial value of the second feature at the calibration time, to obtain normalization results.

The estimating the blood pressure may include applying a weight to each of the normalized results to obtain weighted results, combining the weighted results to obtain combination results, and estimating the blood pressure by applying a scaling factor to the combination result.

The method may further include determining the scaling factor based on at least one of a reference MAP, a reference SBP, and a reference DBP, which are measured at the calibration time, and a result of combining the reference SBP and the reference DBP.

The estimating of the blood pressure may include independently estimating MAP, SBP, and DBP by adjusting at least one of the weight and the scaling factor.

The estimating the blood pressure may include estimating MAP and estimating the DBP and the SBP based on the estimated MAP and a pulse pressure.

The estimating the blood pressure may include estimating MAP of the object by adjusting at least one of the weight and the scaling factor, and estimating DBP and SBP of the object based on the MAP, a pulse pressure measured from the bio-signal, and the adjusted at least one of the weight and the scaling factor.

The estimating the DBP and the SBP may include calculating a first value and a second value based on the pulse pressure, estimating the DBP based on the MAP and the first value, and estimating the SBP based on the DBP and the second value.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
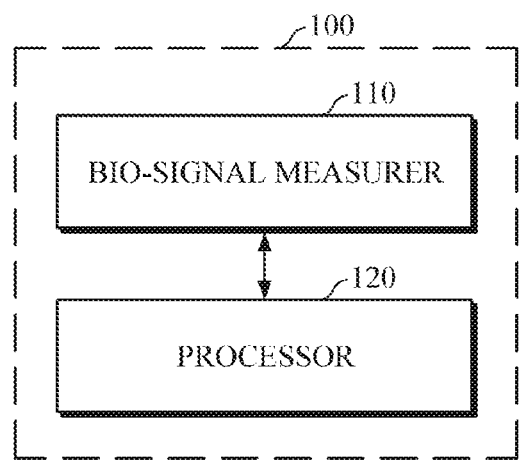
FIG. 1 is a block diagram illustrating an apparatus for estimating blood pressure according to one example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

Hereinafter, an apparatus and method for estimating blood pressure will be described in detail with reference to the accompanying drawings.

FIG. 1 is a block diagram illustrating an apparatus for estimating blood pressure according to an example embodiment. The apparatus 100 for estimating blood pressure of the present embodiment may be mounted in an electronic device, such as a smartphone, a tablet personal computer (PC), a desktop PC, a notebook PC, and the like, or may be fabricated as an independent hardware device. In this case, the independent hardware device may be a wearable device of a wristwatch type, a bracelet type, a wristband type, a ring type, a glasses-type, or a hairband type. However, the hardware device is not limited to the above examples.

Referring to FIG. 1, the apparatus 100 for measuring blood pressure includes a bio-signal measurer 110 and a processor 120.

The bio-signal measurer 110 may include one or more sensors and measure various bio-signals from an object of interest through the sensors. In particular, the sensors may include at least one light emitter and at least one light detector to measure a photoplethysmogram (PPG) signal, an electrocardiography (ECG) signal, an electromyography (EMG) signal, and a ballistocardiogram (BCG) signal. However, the sensors may be realized as a spectrometer, but are not limited thereto.

The processor 120 may receive the bio-signal from the bio-signal measurer 110 and estimate blood pressure based on the received bio-signal. When the processor 120 receives the bio-signal, the processor 120 may extract cardiovascular features that affect blood pressure from the bio-signal, and may estimate blood pressure based on the extracted cardiovascular features. In particular, the cardiovascular features may include a cardiac output (CO) feature as a first feature and a total peripheral resistance (TPR) feature as a second feature. However, the cardiovascular features are not limited thereto.

The processor 120 may estimate blood pressure using reference information acquired from the object at the time of calibration of the bio-signal. Here, the reference information may include reference blood pressure measured at the time of calibration, a reference bio-signal, and a reference cardiovascular feature, for example, a first reference feature and a second reference feature, extracted from the reference bio-signal. In particular, the reference blood pressure may include reference mean arterial pressure (MAP), reference diastolic blood pressure (DBP), and reference systolic blood pressure (SBP).

For example, when the processor 120 extracts the first feature and the second feature from the bio-signal measured by the bio-signal measurer 110 in response to a request for estimating blood pressure, the processor 120 may estimate relative changes of the first feature and the second feature with respect to the first reference feature and the second reference feature, respectively, and estimate blood pressure based on the estimated relative changes of the first feature and the second feature.

Also, in addition to the changes of the first feature and the second feature, the processor 120 may estimate blood pressure by using values calculated from the change of the first feature and the change of the second feature and/or by using other various predefined values together with the changes of the first feature and the second feature. In this case, the values calculated from the changes of the first feature and the second feature may be obtained by multiplying a value indicating the change of the first feature and a value indicating the change of the second feature. Also, the various predefined values may be optimized according to the type of blood pressure (e.g., MAP, DBP, or SBP) to be estimated and/or features of each user.

The processor 120 may independently estimate the MAP, the DBP, and the SBP by adjusting such various values. Alternatively, the processor 120 may first estimate MAP, and then estimate DBP and SBP using the estimated MAP and additional information, such as pulse pressure.

Figure 2:
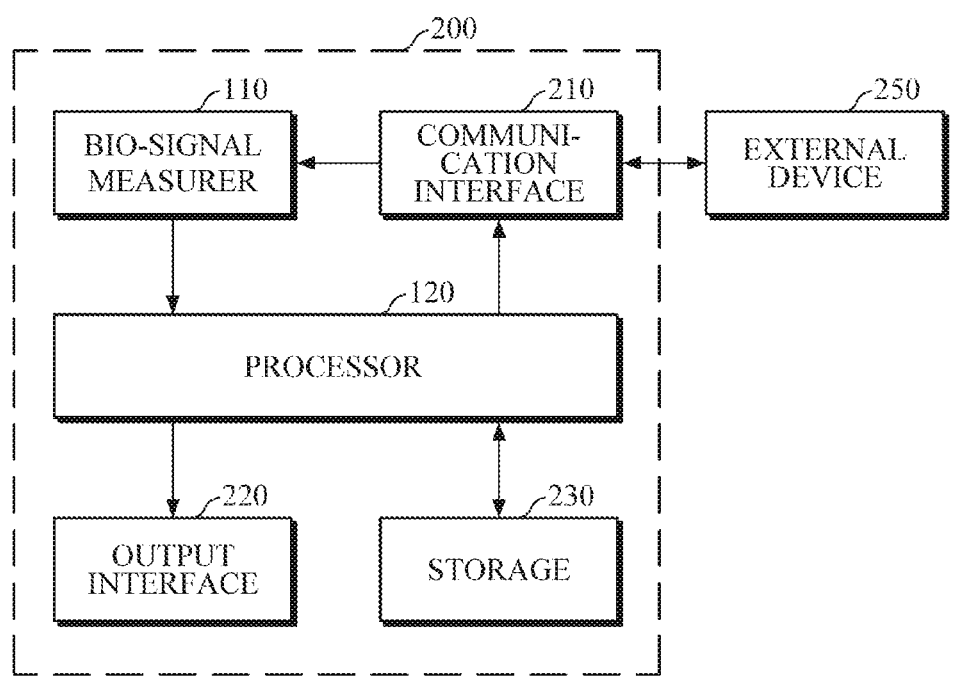
FIG. 2 is a block diagram illustrating an apparatus for estimating blood pressure according to another example embodiment.

FIG. 2 is a block diagram illustrating an apparatus for estimating blood pressure according to another example embodiment.

Referring to FIG. 2, the apparatus 200 for estimating blood pressure may include a bio-signal measurer 110, a processor 120, a communication interface 210, an output interface 220, and a storage 230.

The processor 120 may control the bio-signal measurer 110, the communication interface 210, and the storage 230 in response to a calibration request or a blood pressure estimation request.

For example, when the calibration request is received from the user or a preset calibration condition is satisfied, the processor 120 may control the bio-signal measurer 110 to measure a bio-signal from a user. The bio-signal measurer 110 may measure the bio-signal from the user under the control of the processor 120 and extract a first reference feature and a second reference feature that serve as references for blood pressure estimation from the measured bio-signal.

In addition, when the calibration request is received from the user or the preset calibration condition is satisfied, the processor 120 may also control the communication interface 210 to communicate with an external blood pressure measurement device 250. In this case, the calibration condition may be stored beforehand in the storage 230. For example, it may be preset to perform calibration when a predetermined interval arrives, the number of times that a blood pressure estimated value falls outside a predetermined normal range is greater than or equal to a threshold, or the blood pressure estimated value falls outside the normal range consecutively more than a predetermined number of times.

The communication interface 210 may communicate with the external blood pressure measurement device 250 under the control of the processor 120, and when the user completes blood pressure measurement through the external blood pressure measurement device 250 in order to perform calibration, the communication interface 210 may receive the measured blood pressure information as reference blood pressure.

In this case, the communication interface 210 may communicate with the external blood pressure measurement device 250 using Bluetooth communication, Bluetooth low energy (BLE) communication, near field communication (NFC), a wireless local area network (WLAN) communication, ZigBee communication, infrared data association (IrDA) communication, Wi-Fi direct (WFD) communication, ultra-wideband (UWB) communication, Ant+ communication, WiFi communication, radio frequency identification (RFID) communication, 3rd generation (3G) communication, 4G communication, 5G communication, etc. However, these are merely examples and the types of communication are not limited thereto.

The processor 120 may store the first reference feature and second reference feature extracted for calibration and the reference blood pressure received from the external blood pressure measurement device 250 in the storage 230 as reference information for blood pressure measurement.

Also, when a request for estimating blood pressure is received from the user or the external device 250, the processor 120 may control the bio-signal measurer 110 to measure a bio-signal of the user for blood pressure measurement. When the bio-signal measurer 110 completes the measurement of blood pressure, the processor 120 may estimate a relative change of a cardiovascular feature at the time of estimating blood pressure with respect to the time of calibration by reading reference data at the time of calibration, and estimate blood pressure based on the estimated relative change of cardiovascular feature.

In an example embodiment, when the processor 120 extracts the first feature and the second feature from the bio-signal at an extraction time $T_{extraction}$, and calibrates the first features and the second feature at a calibration time $T_{calibration}$, the processor 120 may estimate a change in the first feature and a change in the second feature which have occurred during a time period from the calibration time $T_{calibration}$ at which the first feature and the second feature are calibrated, to the extraction time $T_{extraction}$ at which the first feature and the second feature are extracted from the bio-signal When the blood pressure estimation is completed, the communication interface 210 may transmit the bio-signal measurement result and/or the blood pressure estimation result to the external device 250, such as a smartphone, a tablet PC, a desktop PC, a notebook PC, a device of a medical institution, or the like.

The output interface 220 may output the bio-signal, the blood pressure estimation result, and additional information associated with the blood pressure estimation result. For example, the output interface 220 may visually provide a variety of information to the user through a display screen. For example, when the blood pressure estimation result is displayed, if the estimated blood pressure falls outside a predetermined normal range, warning information may be displayed to the user by highlighting the result in red color. In another example, a variety of information may be provided to the user in a non-visual manner, such as sound, vibration, tactile sensation, or the like, through a speaker, a haptic motor, or the like. For example, DBP and SBP may be informed by voice. When the estimated blood pressure falls outside the predetermined normal range, the user may be informed of abnormality in health condition through vibration or tactile sensation.

In addition to the above-described reference information, other reference information, the bio-signal, and/or the blood pressure estimation result may be stored in the storage 230. For example, other reference information may include user characteristic information, such as age, sex, health state, or the like of the user, and information, such as a blood pressure estimation equation.

Meanwhile, the storage 230 may include storage media, such as flash memory, hard disk, multimedia card micro type memory, card type memory (e.g., SD or XD memory), random access memory (RAM), static random access memory (SRAM), read-only memory (ROM), electrically erasable programmable read-only memory (EEPROM), magnetic memory, magnetic disk, and optical disk, but is not limited thereto.

An amount of change in mean arterial pressure (MAP) is determined to be proportional to a CO and a TPR as shown in Equation 1.

$$\Delta MAP = CO \times TPR \quad (1)$$

Here, $\Delta$MAP represents a mean arterial pressure difference between the left ventricle and the right ventricle. Generally, mean right ventricular pressure does not exceed 3 to 5 mmHg and may have a similar value to mean left ventricular pressure or mean brachial blood pressure. Therefore, when an absolute CO value and an absolute TPR value are known, it is possible to obtain mean arterial pressure or mean brachial blood pressure. However, it is not easy to estimate the absolute CO value and absolute TPR value based on a bio-signal. According to the present embodiment, it may be possible to estimate an amount of change in blood pressure based on the relative changes in CO and TPR features with respect to the time of calibration.

Values within a range of 0.5 to 0.7 plus/minus from the MAP calculated as described above may be used as the SBP and the DBP. However, the SBP and the DBP may exhibit a decoupling phenomenon in which they do not follow the tendency of change in MAP according to the mechanism of blood pressure change. In addition, in a case where the CO or TPR is greatly changed, such as in a high intensity exercise, the accuracy of blood pressure estimation rapidly deteriorates so that an error of the estimated blood pressure can be greatly increased. Therefore, it may be required to estimate blood pressure by taking into account influence of the mechanism of blood pressure change in order to improve the accuracy of blood pressure estimation. According to the present embodiment, it may be possible to estimate blood pressure based on a relative change in CO and TPR features with respect to the time of calibration, which will be described in detail below, and to stably estimate blood pressure by applying various factors optimized according to the user's characteristics.

Figure 3:
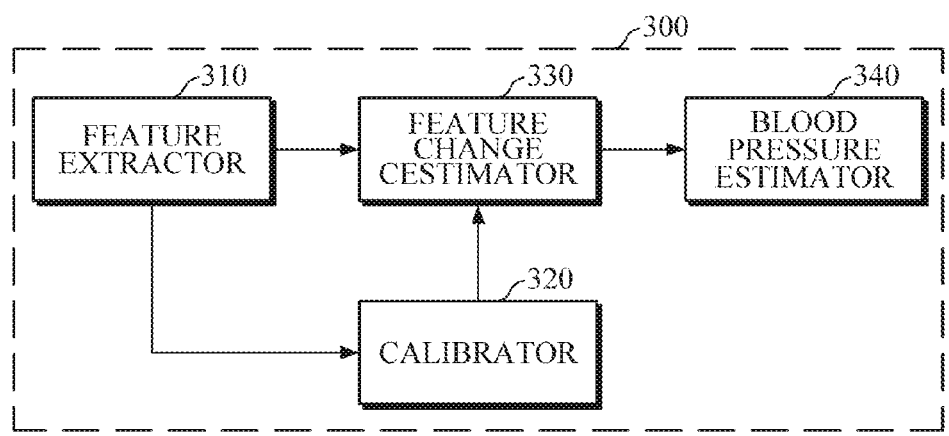
FIG. 3 is a block diagram illustrating a configuration of a processor according to an example embodiment of FIGS. 1 and 2.
Figure 4:
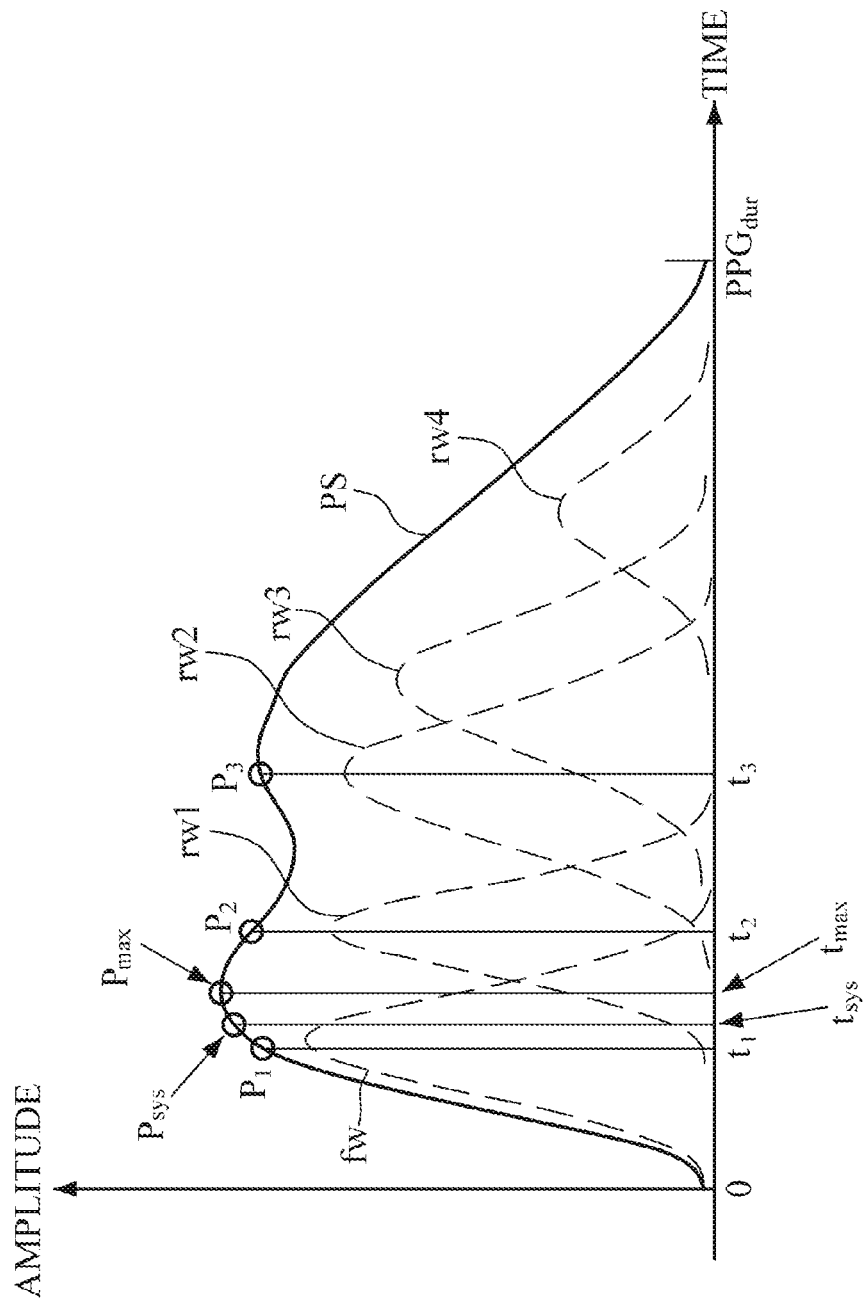
FIG. 4 is a diagram for describing cardiovascular feature extraction.

FIG. 3 is a block diagram illustrating a configuration of a processor according to an example embodiment of FIGS. 1 and 2. FIG. 4 is a diagram for describing cardiovascular feature extraction. An embodiment of blood pressure estimation performed by the processor 300 will be described with reference to FIGS. 3 and 4.

Referring to FIG. 3, the processor 300 may include a feature extractor 310, a calibrator 320, a feature change estimator 330, and a blood pressure estimator 340.

The feature extractor 310 may extract cardiovascular features from various bio-signals measured from a user. In this case, the cardiovascular features may include a first feature including a CO feature and a second feature including a TPR feature.

For example, the feature extractor 310 may acquire heartbeat information from bio-signals, a shape of a bio-signal waveform, the time and amplitude at a maximum point of a bio-signal, the time and amplitude at a minimum point of a bio-signal, the area of a bio-signal waveform, an elapsed time of a bio-signal, the amplitude and time information of a constituent pulse waveform of a bio-signal, and characteristic point information, such as information on internal division points of pieces of the obtained information, and may extract the features using the acquired characteristic point information.

FIG. 4 is a graph illustrating an example of a pulse wave signal among the bio-signals obtained from the user. An example in which the feature extractor 310 extracts features from a pulse wave signal PS will be described with reference to FIG. 4.

As shown in FIG. 4, a pulse wave signal may be formed by a summation of a propagation wave propagating from the heart to peripheral parts and/or blood vessel bifurcations of a body and reflection waves returning from the peripheral parts and/or blood vessel bifurcations. In FIG. 4, a waveform of the measured pulse wave signal is a summation of five constituent pulses, for example, a propagation wave fw and reflection waves rw1, rw2, rw3, and rw4.

The feature extractor 310 may obtain characteristic points from the pulse wave signal by analyzing waveforms of the constituent pulses fw, rw1, rw2, rw3, and rw4. For example, feature extractor 310 may extract the first three constituent pulses fw, rw1, and rw2 to estimate blood pressure based on the three constituent pulses fw, rw1, and rw2. The subsequent pulses may not be observed in some users, may be difficult to detect due to noise, or may often have low correlation with blood pressure estimation.

For example, times $T_1$, $T_2$, and $T_3$ and amplitudes $P_1$, $P_2$, and $P_3$ of maximum points of the first to third constituent pulse waveforms fw, rw1, and rw2 may be obtained as characteristic points. In this case, when a pulse wave signal is obtained, a second-order derivative of the obtained pulse wave signal is computed and the times $T_1$, $T_2$, and $T_3$ and amplitudes $P_1$, $P_2$, and $P_3$ of maximum points of the constituent pulse waveforms fw, rw1, and rw2 may be obtained using the obtained second-order derivative signal. For example, local minimum points are searched from the second-order derivative signal to extract times $T_1$, $T_2$, and $T_3$ corresponding to the first to third local minimum points and the amplitudes $P_1$, $P_2$, and $P_3$ corresponding to the extracted times $T_1$, $T_2$, and $T_3$ may be extracted from the pulse wave signal. Here, the local minimum point refers to a specific point observed in part of a second-order derivative signal at which the signal decreases and then increases again, that is, a downward convex point. However, the embodiment is not limited thereto, such that local maximum points are searched in the second-order derivative signal and times and amplitudes corresponding to the found local maximum points may be used as characteristic points.

In another example, the feature extractor 310 may obtain time $T_{max}$ and amplitude $P_{max}$ at a point in a predetermined period of the pulse wave signal at which the amplitude is maximum as the characteristic points. In this case, the predetermined period may refer to a period from the beginning of the pulse wave signal to a point where the dictoric notch (DN) occurs, which indicates a blood pressure systolic period.

In another example, the feature extractor 310 may obtain time duration $PPG_{dur}$ indicating the total measurement time of the bio-signal or the area PPGarea of the bio-signal waveform as the characteristic points. In this case, the area of the bio-signal waveform may refer to the total area of the bio-signal or the area of the bio-signal corresponding to a predetermined ratio (e.g., 70%) of the entire time duration $PPG_{dur}$.

In still another embodiment, the feature extractor 310 may extract an internally dividing point between two or more characteristic points as the characteristic points. Unstable waveforms of the pulse wave signal may be generated due to non-ideal environment, such as motion noise, sleep, and the like so that the characteristic points may be extracted from wrong positions. In this case, blood pressure measurement may be supplemented by utilizing an internally dividing point between the erroneously extracted characteristic points.

For example, when characteristic points $(T_1, P_1)$ and $(T_{max}, P_{max})$ are obtained from the blood pressure systolic period, it is possible to obtain an internally dividing point $(T_{sys}, P_{sys})$ between the two characteristic points $(T_1, P_1)$ and $(T_{max}, P_{max})$. In this case, weights are applied to time values T1 and Tmax of the two characteristic points $(T_1, P_1)$ and $(T_{max}, P_{max})$, time $T_{sys}$ of the internally dividing point may be obtained using the weighed time values, and an amplitude $P_{sys}$ corresponding to the time $T_{sys}$ of the internally dividing point may be extracted. However, the embodiment is not limited thereto, such that, through the analysis of the obtained bio-signal waveform, an internally dividing point between characteristic points $(T_1, P_1)$ and $(T_2, P_2)$ related to the first and second constituent pulse waveforms fw and $rw_1$ may be obtained from the blood pressure systolic period and an internally dividing point between characteristic points $(T_3, P_3)$ and $(T_4, P_4)$ related to the third and fourth consistent pulse waveforms $rw_2$ and $rw_3$ from the blood pressure diastolic period may be obtained.

The feature extractor 310 may extract a first feature and a second feature by combining various characteristic points obtained from the bio-signal as described above. For example, the first feature and the second feature may be extracted by performing multiplication, division, addition, subtraction, or a combination thereof on the plurality of characteristic points. Alternatively, the first feature and the second feature may be extracted using a function that uses, as an input value, a result of multiplication, division, addition, subtraction, or a combination thereof on the plurality of characteristic points. Here, the function may be a linear function, a quadric function, another multi-dimensional function, a log function, or an exponential function. It is apparent that other types of function can be used. In another example, the first feature and the second feature may be extracted using a function that has at least one characteristic point as an input value. However, the embodiment is not limited thereto.

Meanwhile, the CO feature and the TPR feature may be extracted by combining the characteristic points differently according to the characteristics of the user. In addition, the CO feature and the TPR feature may be individually extracted in accordance with the type of blood pressure by combining the characteristic points differently according to the blood pressure to be extracted, for example, MBP, DBP, and SBP.

When a user's calibration request is received or the preset calibration condition is satisfied as described above, the calibrator 320 may determine whether the calibration has been performed by referring to the calibration condition and, when the calibration is needed, may perform calibration. In this case, when the preset calibration condition is satisfied, the calibrator 320 may guide the user to perform calibration.

When the user measures reference blood pressure through an external blood pressure measurement device 250 for the calibration, the calibrator 320 may obtain the reference blood pressure from the external blood pressure measurement device 250. In addition, the calibrator 320 may control the bio-signal measurer 110 to measure a bio-signal for calibration in response to the user's calibration request.

When the feature extractor 310 extracts the first feature and the second feature from the bio-signal measured at the time of calibration, the calibrator 320 may receive the first feature and the second feature from the feature extractor 310 as a first reference feature and a second reference feature for blood pressure estimation.

The calibrator 320 may store the obtained reference blood pressure, the first reference feature, and the second reference feature, in the storage 230 as reference information for blood pressure estimation, and calibrate an offset in the blood pressure estimation equation using the reference information.

When the bio-signal measurer 110 measures a bio-signal according to the user's blood pressure estimation request or the preset criteria and the feature extractor 310 extracts the first feature and the second feature for blood pressure estimation from the bio-signal, the feature change estimator 330 may estimate a relative change in each of the first feature and the second feature at the time of blood pressure estimation with respect to the time of calibration by utilizing the reference blood pressure, the first reference feature, and the second reference feature, acquired by the calibrator 320. For example, the feature change estimator 330 may estimate the changes in the first feature and the second feature which have occurred during a time period from a calibration time at which the first feature and the second feature are calibrated by the calibrator 320, to an extraction time at which the first feature and the second feature are extracted from the bio-signal.

In one example, the feature change estimator 330 may calculate a first change mount that is an amount of change in the first feature at the time of blood pressure estimation with respect to the first feature at the time of calibration. In addition, the feature change estimator 330 may calculate a second change amount that is an amount of change in the second feature at the time of blood pressure estimation with respect to the second feature at the time of calibration. Also, a third change amount may be calculated using the calculated first and second change amounts. For example, the third change amount may be calculated by multiplying the first change amount and the second change amount. In this case, the third change amount may be a factor for correcting an amount of change in blood pressure that cannot be reflected only by the first feature and the second feature in a blood-pressure changing situation, such as a high-intensity aerobic exercise.

In another example, the feature change estimator 330 may normalize the first change amount, the second change amount, and the third change amount to obtain a first change rate, a second change rate, and a third change rate, respectively. In this case, the feature change estimator 330 may normalize each change amount based on at least one of the first feature and the second feature at the time of calibration. For example, the first change amount may be normalized based on the first reference feature, the second change amount may be normalized based on the second reference feature, and the third change amount may be normalized using the first reference feature and the second reference feature.

The blood pressure estimator 340 may estimate an amount of change in blood pressure based on the relative changes in the first feature and the second feature estimated by the feature change estimator 330. For example, the amount of change in blood pressure may be estimated by combining the first change amount, second change amount, and third change amount calculated by the feature change estimator 330. Alternatively, the amount of change in blood pressure may be estimated by combining the first change rate, second change rate, and third change rate calculated by the feature change estimator 330. In this case, a weight may be applied to each of the change amounts or each of the change rates and then the weighted change amounts or change rates may be combined, and a scaling factor may be additionally applied to the combination result, thereby acquiring a blood pressure measurement result in which the user-specific feature has been reflected.

For example, as shown in Equation 2, the blood pressure estimator 340 may apply a weight to each of the first change rate, the second change rate, and the third change rate, linearly combine the weighted rates, and estimate the amount of change in blood pressure by applying a scaling factor to the linear combination result.

$$\Delta BP = SF_{ad} \times (\alpha \Delta f1_n = \beta \Delta f2_n + \gamma \Delta f3_n) \quad (2)$$

Here, $\Delta BP$ represents an estimated amount of change in blood pressure, and may be MAP, DBP, and SBP. $\Delta f1_n$, $\Delta f2_n$, and $\Delta f3_n$ represent the first change rate, the second change rate, and the third change rate, respectively. $\alpha$, $\beta$, and $\gamma$ represent a weight to be applied to the respective change rates, and may be defined according to the type of blood pressure to be estimated and/or the characteristic of the user. In addition, $SF_{ad}$ represents a scaling factor defined adaptively according to the user's characteristic and/or the type of blood pressure to be estimated. For example, the scaling factor may be a value calculated by combining two or more of reference MAP, reference DBP and reference SBP measured by the external blood pressure measurement device 250 at the time of calibration and a combination thereof.

Meanwhile, according to one example embodiment, the blood pressure estimator 340 may independently estimate an amount of change in each of MAP, DBP, and SBP using Equation 2 above. For example, the amount of change in each blood pressure may be independently estimated using the amount of change or the change rate of each of the first feature and the second feature extracted by the feature extractor 310 according to the type of blood pressure. Alternatively, a weight applied to the amount of change or change rate of each of the features and/or the scaling factor to be applied to the combination result of the amounts of change or the change rates may be set differently according to the type of blood pressure so that the amount of change in each of MAP, DBP, and SBP may be independently estimated. For example, in order to estimate the MAP, a reference MAP of the corresponding user may be used as a scaling factor. Similarly, the reference DBP and the reference SBP may be used as scaling factors for estimating the DBP and the SBP.

In another example, the blood pressure estimator 340 may sequentially estimate the MAP, the DBP, and the SBP. For example, the blood pressure estimator 340 may first estimate an amount of change in MAP using Equation 2 above, and estimate the DBP and SBP using a MAP estimate obtained based on the amount of change in MAP. In this case, the blood pressure estimator 340 may estimate the DBP and the SBP using a pulse pressure along with the MAP estimate. For example, the blood pressure estimator 340 may calculate a first value and a second value based on the pulse pressure, estimate DBP using the MAP estimate and the first value, and estimate SBP using the DBP and the second value.

Equation 3 below shows examples of a function for estimating DBP based on the MAP estimate and a pulse pressure.

$$DBP = MAP - \frac{PP}{3} \qquad (3)$$

$$DBP = MAP - 0.01 \times \exp(4.14 - \frac{40.74}{HR}) \times PP$$

$$SBP = DBP + PP \qquad (4)$$

Here, MAP represents mean arterial pressure, DBP represents diastolic blood pressure, and SBP represents systolic blood pressure. In addition, PP represents a pulse pressure, and HR represents a heart rate. Here, a first value subtracting from the MAP and a second value adding to the DBP are not limited to the above examples, and may be defined variously in consideration of the user's characteristic. The pulse pressure may correspond to the difference between the systolic and diastolic blood pressure, and may represent the force that the heart generates each time it contracts. The pulse pressure may be a previously obtained value. For example, the pulse pressure may be a reference value which is previously obtained by using the estimated SBP and DBP at a calibration time, by using other bio-signal, or by using a pulse pressure measuring device.

Meanwhile, the blood pressure estimator 340 may acquire a pulse pressure by analyzing the measured bio-signal, for example, a pulse wave signal. Alternatively, the blood pressure measurer 340 may receive a measured pulse pressure from a pulse pressure measurement device or may use a preset reference pulse pressure of the user.

When the amount of change in blood pressure is estimated, the blood pressure estimator 340 may estimate blood pressure using a function such as Equation 5 below.

$$BP_{est} = BP_{cal} + \Delta BP \qquad (5)$$

Here, $BP_{est}$ represents a blood pressure estimate, $\Delta BP$ represents an amount of change in blood pressure estimate, and $BP_{cal}$ represents a reference blood pressure at the time of calibration. Here, BP represents MAP, DBP, and SBP.

Figure 5A:
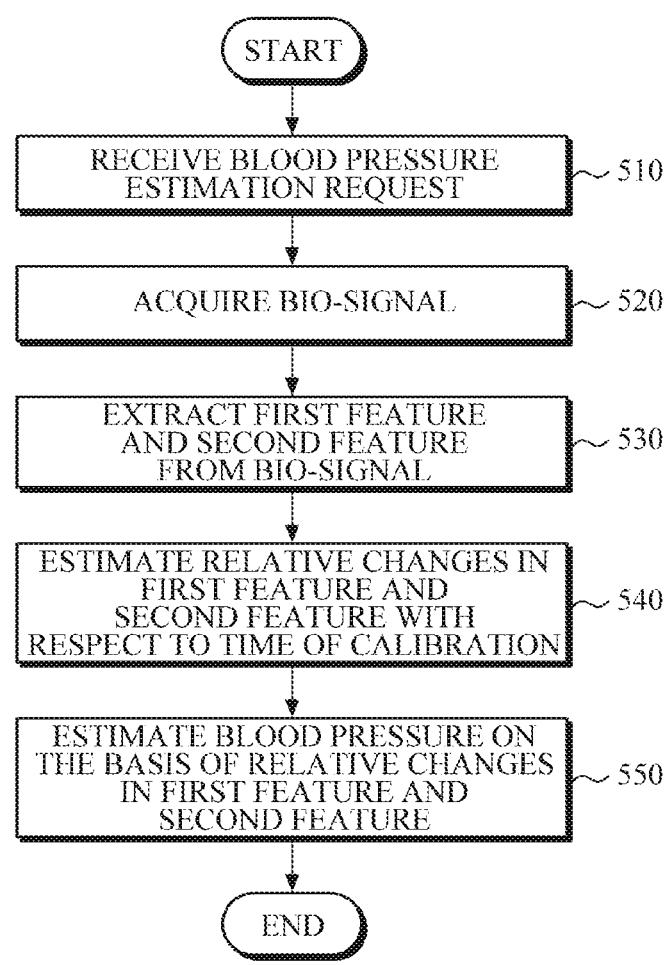
FIGS. 5A and 5B are flowcharts illustrating a method of estimating blood pressure according to an example embodiment.
Figure 5B:
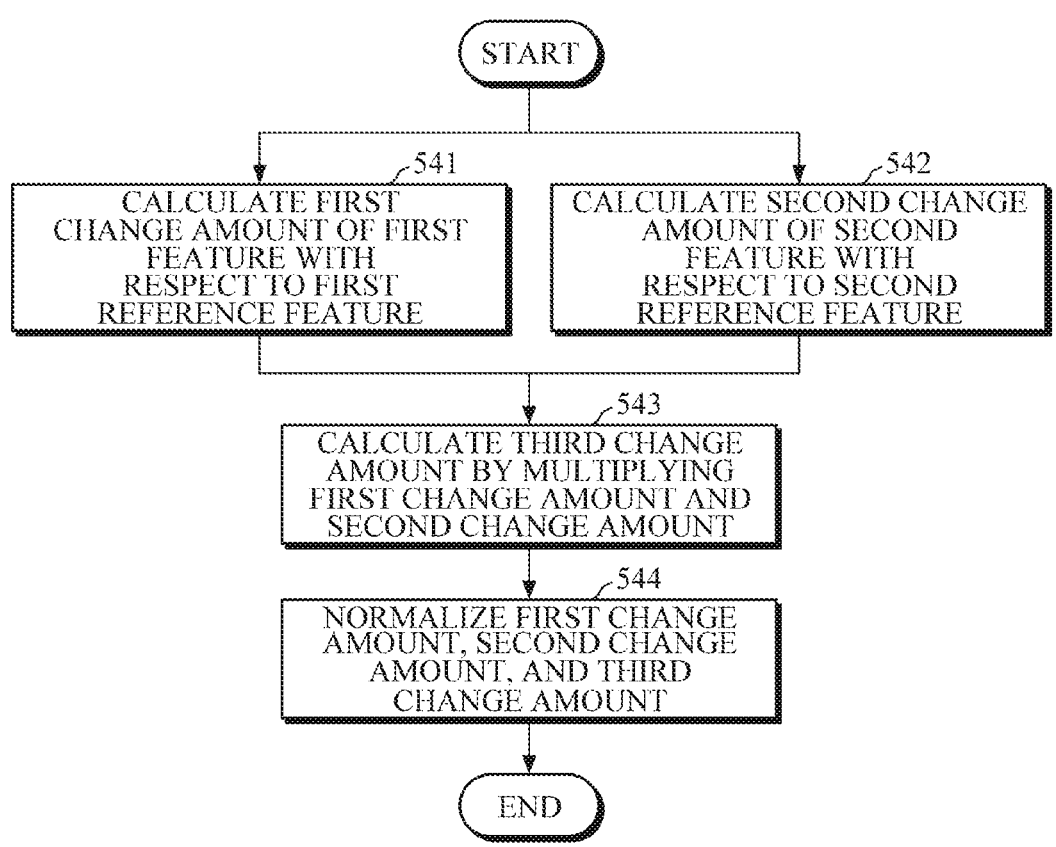

FIG. 5A is a flowchart illustrating a method of estimating blood pressure according to one example embodiment. FIG. 5B is a flowchart illustrating one embodiment of an operation 540 of estimating a relative change of a feature in FIG. 5A.

FIGS. 5A and 5B illustrate a method of estimating blood pressure according to an example embodiment. Various embodiments have been described above in detail, and hence a brief description of the method will be given hereinafter.

The apparatus 100/200 for estimating blood pressure may receive a blood pressure estimation request in operation 510. The apparatus 100/200 may provide an interface to a user and receive the blood pressure estimation request input by the user through the interface. Alternatively, the apparatus 100/200 may establish a communication connection with an external device 250 to receive a blood pressure estimation request from the external device 140. In this case, the external device may be a smartphone, a tablet personal computer (PC), or the like, which the user carries, and the user may control an operation of the apparatus for estimating blood pressure through a device having a superior interface performance or computing performance.

Then, the apparatus 100/200 for estimating blood pressure may control a sensor 110 internally mounted for blood pressure estimation to acquire a bio-signal from the user or receive a bio-signal from an external sensor in operation 520. In this case, the sensor 110 mounted in the apparatus 100/200 and the external sensor 250 may acquire various bio-signals, such as a PPG signal, an ECG signal, an EMG signal, and a BCG signal, from various body parts (e.g., wrist, chest, finger, and the like) of the user.

Then, cardiovascular features may be extracted by analyzing the acquired bio-signal in operation 530. In this case, the cardiovascular features may include a first feature including a CO feature and a second feature including a TPR feature. In this case, the apparatus 100/200 may acquire heartbeat information from bio-signals, a shape of a bio-signal waveform, the time and amplitude at a maximum point of a bio-signal, the time and amplitude at a minimum point of a bio-signal, the area of a bio-signal waveform, an elapsed time of a bio-signal, the amplitude and time information of a constituent pulse waveform of a bio-signal, and characteristic point information, such as information on internal division points of pieces of the obtained information, and may extract the cardiovascular features using the acquired characteristic point information. In this case, the first feature and the second feature may be extracted for each type of blood pressure to be estimated by using different characteristic points or combining two or more different characteristic points.

Then, a relative change in cardiovascular feature at the time of blood pressure estimation with respect to the cardiovascular feature at the time of calibration may be estimated in operation 540. In operation 540, an initial value of a feature may be a value of the feature at a calibration time and a changed value of the feature may be a value of the feature at an extraction time.

For example, referring to FIG. 5B, the apparatus 100/200 for estimating blood pressure may calculate a first change amount of the first feature with respect to the first feature at the time of calibration in operation 541 and calculate a second change amount of the second feature with respect to the second feature at the time of calibration in operation 542.

Then, a third change amount may be calculated by multiplying the first change amount and the second change amount in operation 543. The third change amount calculated as described above may serve to correct a blood pressure estimation error which may occur according to the mechanism of blood pressure change, such as a high-intensity aerobic exercise.

Then, a first change rate, a second change rate, and a third change rate may be calculated by normalizing the first change amount, the second change amount, and the third change amount, respectively in operation 544. In this case, normalization may be performed based on at least one of a first reference feature and a second reference feature at the time of calibration. For example, the first change amount may be normalized based on the first reference feature and the second change amount may be normalized based on the second reference feature. In addition, the third change amount may be normalized using a value obtained by multiplying the first reference feature and the second reference feature.

Referring back to FIG. 5A, the apparatus 100/200 for estimating blood pressure may estimate blood pressure based on a relative change in each of the first feature and the second feature in operation 550. At this time, the relative changes in the first feature and the second feature may be the change amounts calculated in operation 543 or the change rates calculated in operation 544. In one example, the blood pressure may be estimated by linearly combining the change amounts or the change rates. In another example, a weight is applied to each of the change amounts or each of the change rates and the weighted change amounts or change rates are linearly combined, and a scaling factor may be applied to the linear combination result to estimate the blood pressure. Each of the weights and the scaling factor may be defined differently according to the type of blood pressure to be estimated and/or the user's characteristic.

Meanwhile, the apparatus 100/200 for estimating blood pressure may independently estimate MAP, DBP, and SBP by using the relative change in each feature extracted according to the type of blood pressure to be estimated or by controlling each of the weights and/or scaling factor. Alternatively, MAP may be estimated in substantially the same manner as described above, and DBP and SBP may be estimated based on the estimated MAP and a pulse pressure. For example, when the MAP is estimated, a first value and a second value are calculated based on a pulse pressure, DBP may be estimated based on the MAP and the first value, and SBP may be estimated by applying the second value to the DBP. The blood pressure estimation result obtained as described above may be provided to the user in various ways.

Figure 6A:
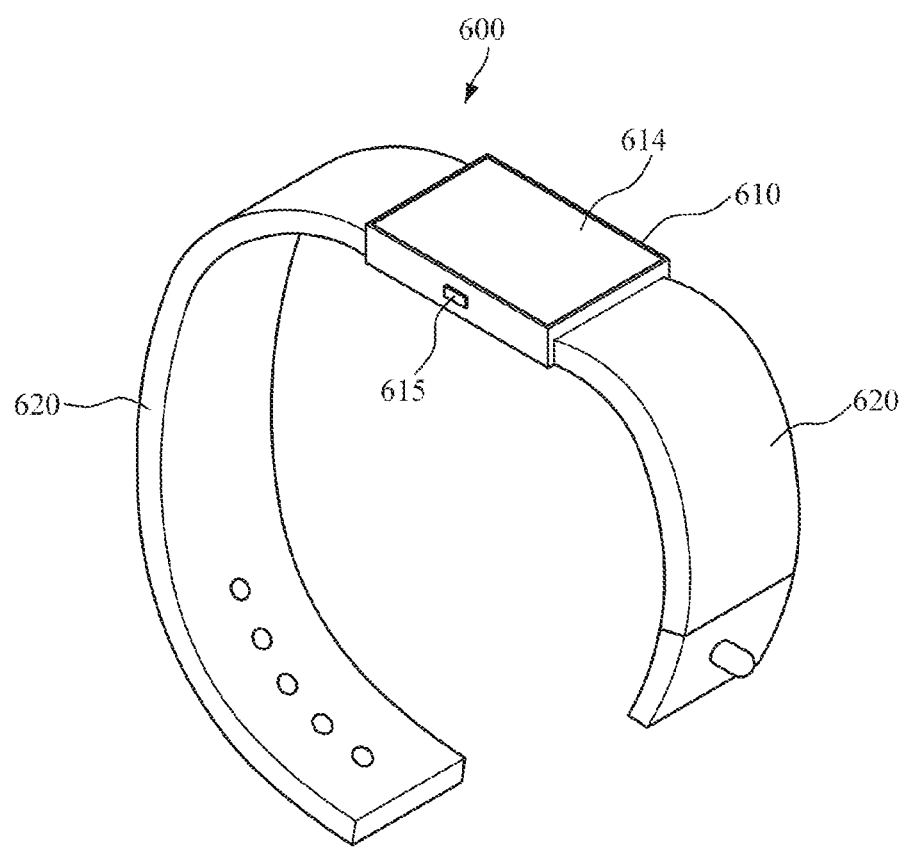
FIGS. 6A and 6B illustrate a wearable device according to an example embodiment.
Figure 6B:
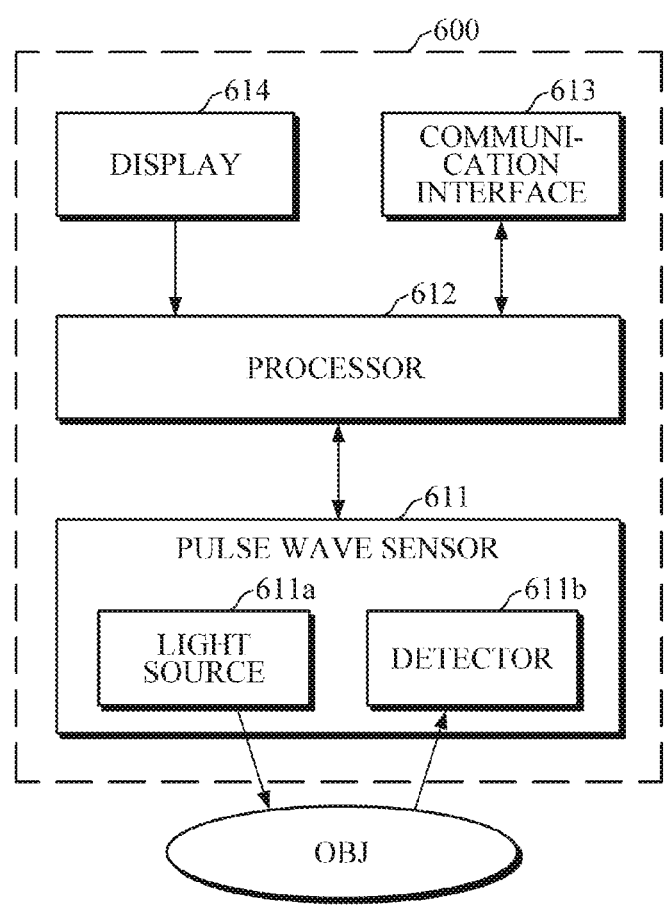

FIGS. 6A and 6B are diagrams for describing a wearable device according to one example embodiment. The above-described various embodiments of the apparatus for estimating blood pressure may be mounted in a smartwatch or a smart band-type wearable device worn on a wrist as illustrated in FIG. 6A. However, the embodiment is not limited thereto, such that the apparatus for estimating blood pressure may be mounted in a smartphone, a tablet PC, a desktop PC, a notebook PC, and the like.

Referring to FIGS. 6A and 6B, the wearable device 600 may include a main body 610 and a strap 620.

The strap 620 may be configured to be flexible and be bendable to wrap around a user's wrist or be separated from the user's wrist. Alternatively, the strap 620 may be configured in the form of an undivided band. In this case, the strap 620 may be filled with air or have an air bag to have elasticity according to a change in pressure applied to the wrist and may transmit the pressure change of the wrist to the main body 610.

A battery may be embedded in the main body 610 or the strap 620 to supply power to the wearable device 600.

In addition, one or more sensors to measure various bio-signals may be mounted inside the main body 610. For example, a pulse wave sensor 611 may be mounted on a rear surface of the main body 610, which is in contact with an object OBJ, for example, a wrist area, in such a manner to be exposed to the object OBJ. The pulse wave sensor 611 may include a light source 611a configured to emit light to the object OBJ and a detector 611b configured to measure a pulse wave signal by detecting light scattered or reflected from the object OBJ. In this case, the light source 611a may include at least one of a light emitting diode (LED), a laser diode, and a phosphor, and may be formed by one or two or more arrays. The light source 611a formed by two or more arrays may be configured to emit light rays of different wavelengths. In addition, the detector 611b may include a photodiode, an image sensor, and the like, and may be formed by one or two or more arrays.

A processor 612 configured to estimate blood pressure based on the bio-signals received from the pulse wave sensor 611 and/or the external sensors may be mounted in the main body 610 of the wearable device 600. The processor 612 may generate a control signal in response to the user's blood pressure estimation request and control the pulse wave sensor 611, and may control a communication interface 613 to receive bio-signals from the external sensor as needed.

The communication interface 613 may be mounted inside the main body 610 and transmit and receive necessary information by communicating with the external device 250 under the control of the processor 612. For example, the communication interface 613 may receive bio-signals from external sensors, such as an ECG sensor, an EMG sensor, a BCG sensor, and the like, which are configured to measure the bio-signals. In addition, the communication interface 613 may receive the blood pressure estimation request from a portable terminal of the user. Also, the communication interface 613 may transmit the extracted characteristic points or feature information to the external device to enable the external device to estimate blood pressure. Additionally, the communication interface 613 may transmit the blood pressure estimation result to the external device 250 to display the result to the user or allow the result to be utilized for various purposes, such as blood pressure history management, disease research, and the like. Further, the communication interface 613 may receive a blood pressure estimation equation or reference information, such as reference blood pressure measured by a blood pressure measurement device, from the external device.

When the bio-signals are received from the pulse wave sensor 611 and/or the external sensors, the processor 612 may extract a CO feature and a TPR feature from the received bio-signals. For example, as described above, the processor 612 may acquire various characteristic points by analyzing the pulse wave signal and extract features by combining the acquired characteristic points. In this case, the processor 612 may extract the CO feature and the TPR feature using MAP, SBP, and DBP.

The processor 612 may estimate relative changes in the CO feature and the TPR feature with respect to those at the time of calibration in consideration of a fact that absolute values of the CO feature and TPR feature at the time of blood pressure estimation are difficult to acquire, and may estimate blood pressure using the estimated relative changes, which has been described in detail above.

The wearable device 600 may further include an operator 615 and a display 614, which are mounted in the main body 610.

The operator 615 may receive a control command of the user and transmit the control command to the processor 612 and may include a power button for inputting a command to power on/off the wearable device 600.

The display 614 may provide a variety of information related to the detected blood pressure to the user under to control of the processor 612. For example, the display 614 may display additional information, such as detected blood pressure, alarm, warning, and the like, to the user using various visual/non-visual methods.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing example embodiments are merely example and are not to be construed as limiting. The present teaching can be readily applied to other types of apparatuses. Also, the description of the example embodiments is intended to be illustrative, and not to limit the scope of the claims, and many alternatives, modifications, and variations will be apparent to those skilled in the art.

What is claimed is:

1. A wearable device comprising:
   a main body comprising a memory, a photoplethysmogram (PPG) sensor, at least one processor, and a display; and
   a strap that is filled with or has an air bag to have an elasticity according to a change in pressure applied to a wrist of a user, and that is configured to transmit the change in pressure to the main body;
   wherein the PPG sensor comprises a light source configured to emit light to the user and a detector configured to obtain a PPG signal by detecting light scattered or reflected from the user;
   wherein the at least one processor is configured to:
      extract a first feature and a second feature from the PPG signal measured at an extraction time, by combining a plurality of characteristic points of the PPG signal, the plurality of characteristic points comprising peak times and peak amplitudes of constituent pulse waveforms of the PPG signal;
      calculate a first difference between an initial value of the first feature at a calibration time before the extraction time and a changed value of the first feature at the extraction time;
      calculate a second difference between an initial value of the second feature at the calibration time and a changed value of the second feature at the extraction time;
      calculate a product of the first difference and the second difference;
      normalize the first difference, the second difference, and the product of the first difference and the second difference, based on at least one of the initial value of the first feature and the initial value of the second feature at the calibration time, to obtain normalization results;
      obtain a combined result of a weighted sum of the normalization results by applying a weight to each of the normalization results and applying a scaling factor to the weighted sum of the normalization results;
      estimate a mean arterial pressure (MAP) of the user by adjusting at least one of the weight and the scaling factor;
      obtain a pulse pressure from the PPG signal; and
      estimate a diastolic blood pressure (DBP) and a systolic blood pressure (SBP) of the user based on the MAP, the pulse pressure, and at least one of the adjusted weight and the adjusted scaling factor,
   wherein the display is configured to provide warning information when the estimated DBP or the estimated SBP falls outside a predetermined range.

2. The wearable device of claim 1, wherein the at least one processor is further configured to acquire, from the PPG signal, at least one of heartbeat information, information on a shape of a waveform of the PPG signal, area information of the waveform, time and amplitude information at a maximum point of the PPG signal, time and amplitude information at a minimum point of the PPG signal, and amplitude and time information of the constituent pulse waveforms of the PPG signal; and extract the first feature and the second feature based on the at least one information.

3. The wearable device of claim 2, wherein the at least one processor is further configured to estimate the MAP the DBP, and the SBP based on the changed value in the first feature and the changed value in the second feature.

4. The wearable device of claim 1, wherein the at least one processor is configured to independently estimate the MAP, the SBP, and the DBP by adjusting at least one of the weight and the scaling factor.

5. The wearable device of claim 1, wherein the at least one processor is further configured to calculate a first value and a second value based on the pulse pressure, estimate the DBP based on the MAP and the first value, and estimate the SBP based on the DBP and the second value.

6. The wearable device of claim 1, further comprising a communication interface circuit configured to, when the user measures a reference blood pressure for calibration through an electrical device at the calibration time, receive the reference blood pressure from the electrical device.

7. A method of operating a wearable device, the method comprising:
   from a strap that is filled with or has an air bag to have an elasticity according to a change in pressure applied to a wrist of a user, transmitting the change in pressure to a main body that comprises a memory, a photoplethysmogram (PPG) sensor, at least one processor, and a display;
   measuring, by the PPG sensor, a PPG signal from the user, wherein the PPG sensor comprises a light source configured to emit light to the user and a detector configured to obtain the PPG signal by detecting light scattered or reflected from the user;
   extracting, by the at least one processor, a first feature and a second feature from the PPG signal measured at an extraction time, by combining a plurality of characteristic points of the PPG signal, the plurality of characteristic points comprising peak times and peak amplitudes of constituent pulse waveforms of the PPG signal;
   calculating, by the at least one processor, a first difference between an initial value of the first feature at a calibration time before the extraction time and a changed value of the first feature at the extraction time, a second difference between an initial value of the second feature at the calibration time and a changed value of the second feature at the extraction time, and a product of the first difference and the second difference;
   normalizing, by the at least one processor, the first difference, the second difference, and the product of the first difference and the second difference, based on at least one of the initial value of the first feature and the initial value of the second feature at the calibration time, to obtain normalization results;
   obtaining, by the at least one processor, a combined result of a weighted sum of the normalization results by applying a weight to each of the normalization results and applying a scaling factor to the weighted sum of the normalization results;
   estimating, by the at least one processor, a mean arterial pressure (MAP) of the user by adjusting at least one of the weight and the scaling factor;

obtaining, by the at least one processor, a pulse pressure from the PPG signal; and estimating, by the at least one processor, a diastolic blood pressure (DBP) and a systolic blood pressure (SBP) of the user based on the MAP, the pulse pressure, and at least one of the adjusted weight and the adjusted scaling factor; and providing, by the display, warning information when the estimated DBP or the estimated SBP falls outside a predetermined range.

8. The method of claim 7, wherein the the MAP, the DBP, and the SBP are estimated based on the changed value in the first feature and the changed value in second feature.

9. The method of claim 7, further comprising determining the scaling factor based on at least one of a reference MAP, a reference SBP, and a reference DBP, which are measured at the calibration time, and a result of combining the reference SBP and the reference DBP.

\* \* \* \* \*